(12) United States Patent
Polak et al.

(10) Patent No.: US 8,679,842 B2
(45) Date of Patent: Mar. 25, 2014

(54) METHOD FOR INCREASING THE POOL OF NGN3+ ENDOCRINE PROGENITOR CELLS AND PANCREATIC ENDOCRINE CELL MASS

(75) Inventors: Michel Polak, Paris (FR); Raphaël Scharfmann, Paris (FR); Samia Zertal-Zidani, Paris (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 250 days.

(21) Appl. No.: 13/203,019

(22) PCT Filed: Mar. 2, 2010

(86) PCT No.: PCT/EP2010/052623
§ 371 (c)(1),
(2), (4) Date: Aug. 24, 2011

(87) PCT Pub. No.: WO2010/100150
PCT Pub. Date: Sep. 10, 2010

(65) Prior Publication Data
US 2011/0319870 A1    Dec. 29, 2011

(30) Foreign Application Priority Data
Mar. 3, 2009   (EP) .................................... 09305197

(51) Int. Cl.
*C12N 5/00*   (2006.01)

(52) U.S. Cl.
USPC ........................................................ 435/377

(58) Field of Classification Search
None
See application file for complete search history.

(56) References Cited

PUBLICATIONS

Chen et al, Nat Chem Biol, Apr. 2009 vol. 5, No. 4, pp. 258-265 (abstract only provided).*
Sheppard et al, J Gen Physiol, 1992), vol. 100, No. 4, pp. 573-591.*
Schultz et al, Am J Physiol, 1996, vol. 271, No. 2 Pt. 1, pp. L192-200.*
Haumaitre, C. et al. "Histone Deacetylase Inhibitors Modify Pancreatic Cell Fate Determination and Amplify Endocrine Progenitors" *Molecular and Cellular Biology*, Oct. 2008, pp. 6373-6383, vol. 28, No. 20, XP-002528419.
Francini, F. et al. "Selective effect of INGAP-PP upon mouse embryonic stem cell differentiation toward islet cells" *Regulatory Peptides*, Feb. 2009, pp. 43-48, vol. 153, XP-002528423.
Jensen, J. et al. "Independent Development of Pancreatic α- and β-Cells from Neurogenin3-Expressing Precursors" *Diabetes*, Feb. 2000, pp. 163-176, vol. 49, XP-001078766.
Burns, C. J. et al. "The in vitro differentiation of rat neural stem cells into an insulin-expressing phenotype" *Biochemical and Biophysical Research Communications*, 2005, pp. 570-577, vol. 326, XP-004679935.
Seino, S. et al. "Diverse Roles of KATP Channels Learned From Kir6.2 Genetically Engineered Mice" *Diabetes*, 2000, pp. 311-318, vol. 49, XP-002971125.
Sunaga, Y. et al. "The effects of mitiglinide (KAD-1229), a new anti-diabetic drug, on ATP-sensitive $K^+$ channels and insulin secretion: comparison with the sulfonylureas and nateglinide" *European Journal of Pharmacology*, Nov. 9, 2001, pp. 119-125, vol. 431, XP-002528420.
Winarto, A. et al. "Morphological Changes in Pancreatic Islets of KATP Channel-Deficient Mice: The Involvement of KATP Channels in the Survival of Insulin Cells and the Maintenance of Islet Architecture" *Arch. Histol. Cytol.*, Feb. 2001, pp. 59-67, vol. 64, No. 1, XP-002528421.
Horie, M. et al. "Insulin secretion and its modulation by antiarrhythmic and sulfonylurea drugs" *Cardiovascular Research*, 1997, pp. 69-72, vol. 34, XP-002528422.
Gradwohl, G. et al. "*neurogenin3* is required for the development of the four endocrine cell lineages of the pancreas" *PNAS*, Feb. 15, 2000, pp. 1607-1611, vol. 97, No. 4, XP-002198929.
Written Opinion in International Application No. PCT/EP2010/052623, Apr. 1, 2010, pp. 1-7.

* cited by examiner

*Primary Examiner* — Allison Ford
(74) *Attorney, Agent, or Firm* — Saliwanchik, Lloyd & Eisenschenk

(57) ABSTRACT

The present invention discloses a method for increasing the pool of Ngn3+ endocrine progenitor cells obtained from stem cells, by contacting said stem cells with a SUR1/Kir6.2 channel inhibitor. The invention also relates to a method for increasing the mass of pancreatic endocrine cells, in particular of β cells. The invention further concerns a method for treating diabetes.

10 Claims, 6 Drawing Sheets

METHOD FOR INCREASING THE POOL OF NGN3+ ENDOCRINE PROGENITOR CELLS AND PANCREATIC ENDOCRINE CELL MASS

CROSS-REFERENCE TO RELATED APPLICATION

This application is the U.S. national stage application of International Patent Application No. PCT/EP2010/052623, filed Mar. 2, 2010, the disclosure of which is hereby incorporated by reference in its entirety, including all figures, tables and amino acid or nucleic acid sequences.

FIELD OF THE INVENTION

The present invention relates to the field of medicine, in particular to treatment or prevention of diabetes. It also relates to the field of cell biology.

BACKGROUND OF THE INVENTION

The pancreas is a gland organ composed of two subclasses of tissue: the exocrine cells (acinar tissue) and the endocrine cells (islets of Langerhans). The exocrine cells produce the digestive enzymes that pass to the small intestine. The islet cells produce hormones which are involved in carbohydrate metabolism. Islets are composed of five cell types: α, β, δ, ε and PP cells which produce glucagon, insulin, somatostatin, ghrelin and pancreatic polypeptide, respectively. β cells secrete insulin in response to an increase in extracellular glucose concentration.

The first morphological signs of the primitive pancreas emerge as dorsal and ventral protrusions of the primitive gut epithelium at embryonic day (E) 9.5 in the mouse. Subsequently, all lineages defining the various pancreatic cell types, comprising endocrine islet and exocrine acinar and duct cells, are formed from a multipotent progenitor cell pool expressing the transcription factor Pdx1. The transcription factor Ngn3 is transiently expressed in a subset of the pancreas progenitor cells from E 9.5 to E 18.5 and initiates the differentiation program of all islet cells. It was demonstrated that Ngn3 is required for the specification of a common precursor for the five pancreatic endocrine cell types (α, β, δ, ε and PP) and mice lacking Ngn3 function fail to generate any pancreatic endocrine cells and die postnatally from diabetes (Gradwohl et al., 2000). The specification of different islet cell types and the completion of the differentiation process require the activation of transcription factors that are downstream of Ngn3. Among these regulatory factors NeuroD1, Pax4 and Nkx2.2 are direct targets of Ngn3.

Type 1 and type 2 diabetes are characterized by loss and dysfunction of β cells. Type 2 diabetes, which is the most common form, is associated with a gradual decline in sensitivity to insulin. Type 1 diabetes is a condition in which the body's immune cells attack β cells located in pancreatic islets, reducing or eliminating the body's ability to produce insulin. Treatment for type 1 diabetes is a lifelong commitment of monitoring blood glucose, exercising, dieting, and taking insulin. In some cases, individuals with type 2 diabetes similarly require insulin therapy. However, these approaches are sometimes insufficient to control blood glucose levels. Poorly controlled diabetes can lead to potentially fatal complications. Eyes, nerves and kidneys are particularly susceptible to the damage caused by poorly controlled type 1 or type 2 diabetes.

An alternative treatment for patients with type 1 diabetes is whole organ pancreatic transplant. Such a procedure offers the possibility of excellent glycemic control but patients are subjected to the adverse effects of immunosuppression and the risks of major surgery.

Recently great strides have been made in developing human islet transplantation in the treatment of diabetes. However, a large number of islets is required to achieve long-term insulin independence and two or far more donor organs are needed to accumulate enough islet cells for a single complete transplant. Thus, the lack of cadaveric human islets is a major obstacle in the widespread use of islets transplantation. Furthermore, with this procedure, immunosuppression is still necessary and the islets are often severely injured from storage conditions or transport time causing apoptosis of the insulin secreting β cells.

These limitations have given a high priority to efforts to stimulate the growth of new pancreatic islet tissue. As example, the patent application WO 2006/046923 proposes to treat pancreatic stem cells with retinoic acid to obtain pancreatic hormone-producing endocrine cells.

Nevertheless, there is still a strong need to provide methods for providing large number of β cells which could be used to treat diabetes by pancreatic islet transplantation or for promoting β cell maturation.

SUMMARY OF THE INVENTION

In a first aspect, the present invention provides an in vitro method for increasing the pool of Ngn3+ endocrine progenitor cells obtained from stem cells, wherein said method comprises the step of contacting stem cells having the capacity to differentiate into pancreatic endocrine cells, except human embryonic stem cells, with a SUR1/Kir6.2 channel inhibitor.

In a second aspect, the present invention provides an in vitro method for increasing the number of pancreatic endocrine cells obtained from stem cells, wherein said method comprises the step of contacting stem cells having the capacity to differentiate into pancreatic endocrine cells, except human embryonic stem cells, with a SUR1/Kir6.2 channel inhibitor.

In another aspect, the present invention also concerns an in vitro method for increasing the β cell mass obtained from stem cells, wherein said method comprises the step of contacting stem cells having the capacity to differentiate into pancreatic endocrine cells with a SUR1/Kir6.2 channel inhibitor.

The present invention also concerns an in vitro method for obtaining pancreatic endocrine cells, wherein said method comprises the step of contacting stem cells having the capacity to differentiate into pancreatic endocrine cells with a SUR1/Kir6.2 channel inhibitor.

In a further aspect, the present invention provides the use of a SUR1/Kir6.2 channel inhibitor for the in vitro or ex vivo differentiation of stem cells into pancreatic endocrine cells.

In another aspect, the present invention provides pancreatic cells obtained by the method of the invention.

In a further aspect, the present invention concerns pancreatic islets obtained by the method of the invention.

In another aspect, the present invention concerns a pharmaceutical composition comprising pancreatic cells and/or pancreatic islets obtained by the method of the invention.

In another aspect, the present invention concerns pancreatic cells and/or pancreatic islets obtained by the method of the invention for the treatment of diabetes in a subject in need thereof.

In a last aspect, the present invention concerns a method of treating diabetes in a subject in need thereof, said method comprising steps consisting of obtaining stem cells having the capacity to differentiate into pancreatic endocrine cells;

contacting said stem cells with a SUR1/Kir6.2 channel inhibitor during their differentiation into pancreatic endocrine cells;

transplanting a therapeutically effective amount of pancreatic islets obtained by differentiation of said stem cells into said subject.

BRIEF DESCRIPTION OF THE DRAWINGS

FIG. 1: Morphological effect of increased concentrations of glibenclamide on embryonic pancreas development in vitro.

Quantification by real-time PCR of insulin.

α cell differentiation was evaluated by glucagon staining in E13.5 pancreases cultured 7 days in presence or in absence of 100 µM glibenclamide.

FIG. 3: Glibenclamide treatment amplifies the pool of pro-endocrine precursors without acting on pancreatic progenitor proliferation.

DETAILED DESCRIPTION OF THE INVENTION

Figure 1A:
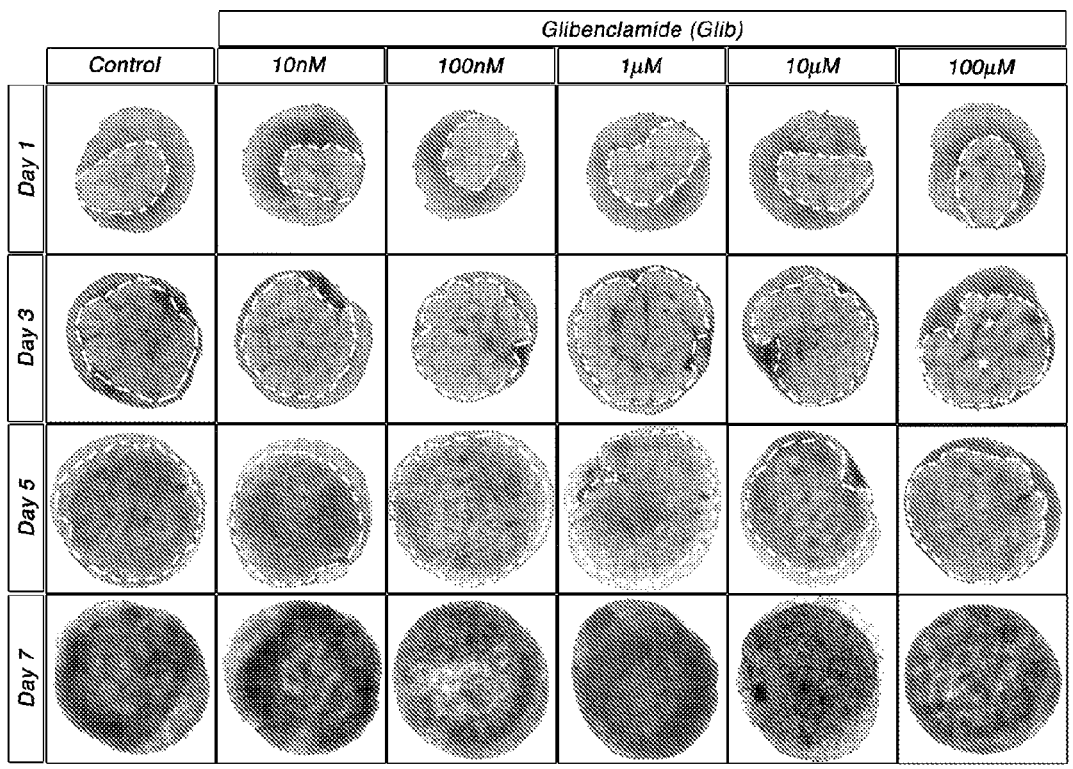
(FIG. 1A) E13.5 embryonic Rat pancreases were cultured at the air/liquid interface for 7 days without (control) or with increased concentrations of glibenclamide. Representative pictures of 1, 3, 5 and 7 days-cultured pancreases are shown. The epithelium, circled in white and surrounded by its mesenchyme, is more branched in the 100 µM glibenclamide-treated pancreases (white asteriks).

The pancreatic β cell $K_{ATP}$ channel plays a key role in glucose stimulated-insulin secretion by regulating the flux of potassium ions across cell membranes. $K_{ATP}$ channels are open at low glucose concentrations but close when glucose uptake and metabolism are stimulated by an increase in the plasma glucose concentration. This leads to membrane depolarization, activation of voltage-dependent calcium channels, calcium influx and, in turn, insulin secretion. This channel is composed of two types of subunit—the inward rectifier $K^+$ channel (Kir6.2) which forms the channel pore, and the sulfonylurea receptor (SUR1), which serves as a regulatory subunit. These subunits associate with a stoichiometry of $Kir6.2_4/SUR1_4$. Kir6.2 and SUR1 subunits are encoded by KCNJ11 and ABCC8 genes, respectively.

The inventors have herein demonstrated that SUR1/Kir6.2 channel inhibitors are able to amplify the pool of endocrine progenitor Ngn3+ cells which subsequently differentiate into pancreatic endocrine cells. These inhibitors can thus be used to dramatically increase the β cell mass and insulin secretion capacity in a developing pancreas or islet.

In a first aspect, the present invention provides an in vitro method for increasing the pool of Ngn3+ endocrine progenitor cells, wherein said method comprises the step of contacting stem cells having the capacity to differentiate into pancreatic endocrine cells with a SUR1/Kir6.2 channel inhibitor.

As used herein, the term "Ngn3+ endocrine progenitor cells" refers to precursors of pancreatic endocrine cells expressing the transcription factor Neurogenin-3 (Ngn3). Progenitor cells are more differentiated than multipotent stem cells and can differentiate into only few cell types. In particular, Ngn3+ endocrine progenitor cells have the ability to differentiate into the five pancreatic endocrine cell types (α, β, δ, ε and PP). The expression of Ngn3 may be assessed by any method known by the skilled person such as immunochemistry using an anti-Ngn3 antibody or quantitative RT-PCR.

The term "stem cells" refers to cells which have the ability to go through numerous cycles of cell division while maintaining an undifferentiated state and have the capacity to differentiate into specialized cell types. There are two broad types of mammalian stem cells: embryonic stem cells isolated from the blastocysts and adult stem cells found in adult tissues.

Stem cells may be classified according to their potency (their ability to differentiate into different cell types). Totipotent stem cells can differentiate into embryonic and extraembryonic cell types. Such cells contain all the genetic information needed to create a complete and viable organism. Pluripotent stem cells can differentiate into nearly all cell types but cannot develop into an embryo. These cells maintain the plasticity to generate all types of cells in an individual, except extraembryonic tissue such as placenta. Multipotent stem cells can differentiate into a number of cell types, but only those of a closely related family of cells. Adult stem cells, which reside in small number in almost all adult tissues, are generally multipotent: their regenerative potential is tissue or germ-layer specific.

As used herein, the term "stem cells" encompasses embryonic stem cells, adult stem cells and reprogrammed somatic cells (induced pluripotent stem cells).

In a particular embodiment, embryonic stem cells are non-human embryonic stem cells due to some patent law and practices.

In an embodiment, stem cells having the capacity to differentiate into pancreatic endocrine cells are selected from the group consisting of pancreatic stem cells, pluripotent stem cells and multipotent stem cells.

In a particular embodiment, pancreatic stem cells are selected from the group consisting of stem cells derived from pancreatic islets, pancreatic ducts, pancreatic acinar cells and stem cells derived from the dorsal pancreatic bud from embryos.

As used herein, the term "cells derived from" shall be taken to indicate that this particular group of cells has originated from the specified source, but has not necessarily been obtained directly from said source.

As used herein, the term "pancreatic stem cells" refers to multipotent and organ specific stem cells expressing Pdx1 and which are able to differentiate into all types of pancreatic cells. The pancreas duodenal homeobox gene Pdx1 (UniGene Hs.32938) is one of the earliest genes expressed in the developing pancreas. Cells expressing Pdx1 give rise to all three types of pancreatic tissue, exocrine, endocrine and duct. After birth, Pdx1 expression is essentially restricted to β cells within the endocrine islets of the pancreas.

The identification of pancreatic stem cells from pancreatic islet and ductal populations has been described in Seaberg et al. (Seaberg et al., 2004). This paper demonstrated that these stem cells coexpress neural and pancreatic precursor markers and differentiate to form distinct populations of neurons, glial and stellate cells, pancreatic endocrine beta-, alpha- and delta-cells, and pancreatic exocrine cells.

Furthermore, it was recently found that pancreatic ductal and acinar cells are able under certain conditions to regress to a less differentiated phenotype and then can differentiate to form endocrine cells and, in particular, to form β cells (Bonner-Weir et al., 2008; Minami et al., 2008).

Consequently, stem cells having the capacity to differentiate into pancreatic endocrine cells may be pancreatic stem cells derived from exocrine, endocrine or ductal tissue or differentiated pancreatic cells which move into a less differentiated stage to express Pdx1. Such pancreactic stem cells may be obtained from adult tissue by any method known in the prior art such as those described in the articles of Seaberg et al. Bonner-Weir et al., and Minami et al. (Seaberg et al., 2004 Bonner-Weir et al., 2008; Minami et al., 2008).

Pancreatic stem cells may also be derived from the dorsal pancreatic bud from embryos. The dorsal pancreas is an embryonic bud from the endodermal lining of the gut on the dorsal wall cephalad to the level of the hepatic diverticulum, which forms most of the pancreas and its main duct. Pancreatic stem cells expressing Pdx1 may be obtained from fertilized ovocytes when pancreatic tissue has started to develop and before the terminal differentiation of most pancreatic cells.

In an embodiment, pancreatic stem cells are derived from human embryos. The age of these embryos is between 2 and 12 weeks of development, preferably between 2 and 8 weeks and more preferably between 2 and 6 weeks of development.

In a particular embodiment, pancreatic stem cells are derived from the dorsal pancreatic bud from non-human embryos due to some patent law and practices.

In another embodiment, stem cells having the capacity to differentiate into pancreatic endocrine cells are multipotent stem cells derived from other adult tissue than pancreatic tissue. Preferably, multipotent stem cells are derived from adult tissue selected from the group consisting of bone marrow, liver, central nervous system, spleen and adipose tissue.

Bone marrow-derived stem cells (hematopoietic or mesenchymal) have been described to be able to differentiate into pancreatic endocrine cells (Oh et al., 2004; Moriscot et al., 2005; Sun et al., 2007; Gabr et al., 2008). Bone marrow-derived stem cells may be isolated from the bone marrow based on their ability to adhere to plastic support. Then, they may be expanded and cultured. Pdx-1 gene expression may be induced in these cells using factors such as dimethyl sulfoxide, trichostatin or β-mercaptoethanol.

Mesenchymal stem cells from bone marrow and adipose tissue represent a very similar cell population with comparable phenotype. Consequently, adipose tissue-derived mesenchymal stem cells have also the potential to differentiate in pancreatic endocrine cells (Timper et al., 2006).

Liver stem cells, also named oval stem cells, have been described to be able to differentiate into pancreatic endocrine cells when cultured in a high-glucose environment (Yang et al., 2002). Another possibility may be to induce transdifferentiation of liver stem cells into pancreatic progenitor cells by expressing a Pdx-1 transgene (Sapir et al., 2005).

Brain-derived neural progenitor cells (Hori et al., 2005) and splenocytes (Kodama et al., 2003) have been also described to be able to differentiate into pancreatic endocrine cells.

In a preferred embodiment, multipotent stem cells derived from adult tissue and having the capacity to differentiate into pancreatic endocrine cells are not genetically modified. These cells exhibit the capacity to differentiate into pancreatic endocrine cells only by culturing them in presence of specific growth factors and/or compounds.

In a further particular embodiment, stem cells are pluripotent stem cells obtained by reprogramming of somatic cells. Such cells are also named induced pluripotent stem cells.

It has been found that induced pluripotent stem cells recapitulated the features of embryonic stem cells, such as human embryonic stem cells, and are thus an alternative to the controversial use of these cells (Romano et al., 2008). Induced pluripotent stem cells may be obtained from somatic cells, such as human skin fibroblasts, by a variety of methods essentially based on manipulation of a selected group of transcription factors (Maherali et al., 2008). For instance, induced pluripotent stem cells have been generated by ectopic expression of four transcription factors, OCT4, SOX2, KLF4 and c-MYC (Takahashi et al., 2007; Lowry et al., 2008) or OCT4, SOX2, NANOG and LIN28 (Yu et al., 2007). Furthermore, it has been demonstrated that induced pluripotent cells have the potential to differentiate into pancreatic endocrine cells (Tateishi et al., 2008).

In another embodiment, pluripotent stem cells are derived from embryonic stem cells.

Embryonic stem (ES) cells are derived from totipotent cells of the early mammalian embryo and are capable of unlimited, undifferentiated proliferation in vitro. Essential characteristics of these cells include (i) derivation from the preimplantation or periimplantation embryo, (ii) prolonged undifferentiated proliferation, and (iii) stable developmental potential to form derivatives of all three embryonic germ layers (endoderm, mesoderm and ectoderm) even after prolonged culture.

For human embryonic stem cells, it has been demonstrated that these cells may be obtained from frozen-thawed blastocysts that were destined to be discarded after 5 years in a routine human IVF-embryo transfer programme (Park et al., 2004).

ES cells grow as homogenous and undifferentiated colonies when they are propagated on a feeder layer such as mouse embryonic fibroblasts. Removal from this feeder layer is associated with differentiation into derivatives of the three embryonic germ layers. Human embryonic stem cells have been described to be able to differentiate in vitro into pancreatic endocrine cells, and particularly into β cells (Assady et al., 2001).

In a particular embodiment, pluripotent stem cells are derived from non-human embryonic stem cells, due to some patent law and practices.

Stem cells as described above, which have the capacity to differentiate into pancreatic endocrine cells and thus into their precursors, namely Ngn3+ endocrine progenitor cells, may be used in the method of the invention for increasing the pool of these Ngn3+ cells. The step of contacting with a SUR1/Kir6.2 channel inhibitor has to be conducted after detection of pdx1 gene expression and before the complete differentiation of these cells into pancreatic endocrine cells, preferably after detection of pdx1 gene expression and before detection of Ngn3 expression.

Stem cells as described above may be derived from any mammalian such as mice, rats, pigs, dogs, cats, horses, monkeys or humans.

The term "SUR1/Kir6.2 channel inhibitor" as used herein refers to a compound which has the capacity to close the SUR1/Kir6.2 channel and thus to block the flux of potassium ions across cell membranes In an embodiment, the SUR1/Kir6.2 channel inhibitor is selected from sulfonylureas and metiglinides (or glinides), and any combination thereof.

In one embodiment, the inhibitor is a sulfonylurea selected from the group consisting of acetohexamide, carbutamide, glibornuride, chlorpropamide, tolbutamide, tolazamide, glipizide, gliclazide, glibenclamide (glyburide), gliquidone, glyclopyramide, glisoxepide and glimepiride.

In another embodiment, the inhibitor is a metiglinide selected from the group consisting of repaglinide, nateglinide and mitiglinide.

In a preferred embodiment, the SUR1/Kir6.2 channel inhibitor is glibenclamide.

The SUR1/Kir6.2 channel inhibitor may be used alone, in combination with one or several SUR1/Kir6.2 channel inhibitors and in combination with other active substances. For example, glibenclamide may be used in association with metformine.

In the present method, stem cells having the capacity to differentiate into pancreatic endocrine cells are contacted with a SUR1/Kir6.2 channel inhibitor. This step of contacting stem cells with a SUR1/Kir6.2 channel inhibitor may consist of culturing stem cells in a medium containing a SUR1/Kir6.2 channel inhibitor.

The concentration of the SUR1/Kir6.2 channel inhibitor may be chosen by the skilled person using well known methods. For instance, preliminary tests may be achieved to evaluate the toxicity of the SUR1/Kir6.2 channel inhibitor on stem cells. In this case, stem cells are cultured with different concentrations of this inhibitor and toxicity markers are followed. These markers may be markers of apoptotic cell death such as apoptotic DNA fragmentation and DEVD-caspase activation. The concentration of the channel inhibitor has to be chosen in order to be safe of any toxic effects on growing stem cells. Preferably, the concentration is chosen in order to be the highest concentration without any toxic effect.

In an embodiment, stem cells are contacted with a SUR1/Kir6.2 channel inhibitor by culturing them in presence of 0.1 to 500 μM of said inhibitor, preferably in presence of 1 to 250 μM of said inhibitor and the most preferably in presence of 50 to 150 μM said inhibitor.

In a particular embodiment, the SUR1/Kir6.2 channel inhibitor is glibenclamide and stem cells are contacted with glibenclamide by culturing them in presence of 100 μM of glibenclamide.

The culture medium which may be used during the step of contacting with a SUR1/Kir6.2 channel inhibitor is designed to support the growth and the differentiation of stem cells. This medium generally is changed every day and comprises a carbon source, a nitrogen source, antibiotics to prevent fungi and bacteria growth, a buffer to maintain pH and specific growth factors. This medium may be easily designed by the skilled person in the art. An example of such medium is presented in the experimental section below or in the experimental section of the article of Guillemain et al (Guillemain et al., 2007).

Other compounds may also be added in the medium such as compound known to stimulate β cell replication, to induce differentiation into β cells or to inhibit apoptosis of β cells. Such compounds may be chosen from the group consisting of nicotinamide, glucagon-like peptide-1 (GLP-1), glucose, exendin-4 and retinoic acid.

In an embodiment, stem cells are contacted with a SUR1/Kir6.2 channel inhibitor during 3 to 10 days, preferably from 5 to 7 days. During the step of contacting, stem cells are cultured in a medium supporting growth and differentiation and containing a SUR1/Kir6.2 channel inhibitor.

At the end of the step of contacting and/or several days later, the number of Ngn3-expressing cells may be assessed in order to verify the efficiency of the treatment, i.e. the increase of the pool of Ngn3+ endocrine progenitor cells. The number of Ngn3-expressing cells obtained in treated samples is compared to the number of Ngn3-expressing cells obtained in control sample, i.e. without step of contacting with a SUR1/Kir6.2 channel inhibitor. In order to be comparable, stem cells in treated and control samples have to be of the same cellular type and submitted to the same protocol except channel inhibitor treatment.

In an embodiment, the pool of Ngn3+ endocrine progenitor cells has increased by more than 25%, preferably by more than 50% and the most preferably by more than 100%.

In a preferred embodiment, the pool of Ngn3+ endocrine progenitor cells has increased by more than 150%, preferably by more than 200% and the most preferably by more than 250%.

In an embodiment, the method further comprises a step consisting of the differentiation of obtained Ngn3+ endocrine progenitor cells into precursors of pancreatic endocrine cells and/or pancreatic endocrine cells.

In appropriate culture medium, such as described above, Ngn3+ endocrine progenitor cells differentiate into precursors of pancreatic endocrine cells and subsequently into β, δ, ε and/or PP cells.

The present invention also concerns an in vitro method for increasing the number of pancreatic endocrine cells obtained from stem cells, wherein said method comprises the step of contacting stem cells having the capacity to differentiate into pancreatic endocrine cells with a SUR1/Kir6.2 channel inhibitor.

In a particular embodiment, this method comprises the step of contacting stem cells having the capacity to differentiate into pancreatic endocrine cells, except human embryonic stem cells, due to some patent law and practices.

The present invention also concerns an in vitro method for increasing the β cell mass obtained from stem cells, wherein said method comprises the step of contacting stem cells having the capacity to differentiate into pancreatic endocrine cells with a SUR1/Kir6.2 channel inhibitor.

In a particular embodiment, this method comprises the step of contacting stem cells having the capacity to differentiate into pancreatic endocrine cells, except human embryonic stem cells, due to some patent law and practices.

The present invention also concerns an in vitro method for obtaining pancreatic endocrine cells, wherein said method comprises the step of contacting stem cells having the capacity to differentiate into pancreatic endocrine cells with a SUR1/Kir6.2 channel inhibitor.

In another aspect, the present invention concerns the use of a SUR1/Kir6.2 channel inhibitor for the in vitro or ex vivo differentiation of stem cells into pancreatic endocrine cells. Stem cells have to be able to differentiate into pancreatic endocrine cells and may be chosen as described above.

In another aspect, the present invention also provides an in vivo method for increasing the number of pancreatic endocrine cells, in particular of β cells, in the pancreas of a foetus, wherein said method comprises administering a SUR1/Kir6.2 channel inhibitor to the pregnant female.

In another aspect, the present invention also provides an in vivo method for increasing the number of pancreatic endocrine cells, in particular of β cells, in the pancreas of a subject, wherein said method comprises administering a SUR1/Kir6.2 channel inhibitor to said subject. Preferably, the subject is a child.

In a further aspect, the present invention provides pancreatic cells obtained by the in vitro method of the invention.

In an embodiment, pancreatic cells are Ngn3$^+$ endocrine progenitor cells.

In another embodiment, pancreatic cells are cells derived from Ngn3$^+$ endocrine progenitor cells, i.e. pancreatic endocrine cell precursors and pancreatic endocrine cells.

Precursors of pancreatic endocrine cells may express, for instance, Pax4 (paired box-encoding gene 4) or Arx (Aristaless-related homeobox).

Pancreatic endocrine cells may be α, β, δ, ε and/or PP cells.

In a preferred embodiment, pancreatic cells are β cells. The term "β cells", as used herein, refers to pancreatic cells which are able to produce insulin. In vivo, these cells are found in the pancreatic islets of Langerhans. This cell population may be identified by the expression of specific markers such as ZnT-8, a specific zinc transporter (Chimienti et al. 2004) or MafA, a specific transcription factor (Zhang et al., 2005; Matsuoka et al., 2007), or by an ability to respond to glucose challenge in a specific way by secreting insulin.

The present invention also concerns pancreatic islets comprising pancreatic cells of the invention as described above.

As used herein, the term "pancreatic islet" refers to cell small discrete cell aggregates obtained in vitro or ex vivo and including pancreatic endocrine hormone producing cells, such as α cells, β cells, δ cells, PP cells and ε cells. Pancreatic islets resemble the form of islets of Langerhans of the pancreas and are spheroid in form. In vivo, the islets of Langerhans are surrounded by the pancreatic exocrine tissue.

In an embodiment, pancreatic islets comprise β cells obtained by the method of the invention.

In another embodiment, pancreatic islets comprise β cells and α cells obtained by the method of the invention.

In a preferred embodiment, pancreatic islets comprise α cells, β cells, δ cells, PP cells and ε cells obtained by the method of the invention.

In a further aspect, the present invention concerns a pharmaceutical composition comprising pancreatic cells and/or pancreatic islets of the invention, and a pharmaceutically acceptable carrier.

Pharmacologically acceptable carriers have to be compatible with the cells and may be, for instance, cell culture medium (such as Eagle's minimal essential media), phosphate buffered saline, Krebs-Ringer buffer, and Hank's balanced salt solution +/− glucose (HBSS).

In a preferred embodiment, pharmaceutical composition is suitable for parenteral administration, e.g. subcutaneously, retroperitoneally and intravenously. Such composition may comprise any additive compatible with the cells.

The pharmaceutical composition comprising pancreatic cells and/or pancreatic islets of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. The compositions for parenteral administration are generally physiologically compatible sterile solutions or suspensions. Adjuvants such as a local anesthetic, preservative and buffering agents can be dissolved in the vehicle.

In one embodiment, the pharmaceutical composition comprises pancreatic cells and/or pancreatic islets of the invention encapsulated in a biocompatible matrix known in the art. A variety of encapsulation technologies have been developed (e.g. Qi et al., 2008 and WO 91/10425).

The pharmaceutical composition comprising pancreatic cells and/or pancreatic islets of the invention, may be used for islet transplantation and/or treatment of type 1 and type 2 diabetes.

The pharmaceutical composition can also comprise one or several additional active compounds, e.g. compounds known to enhance cell survival, proliferation or to prevent any contamination.

In another aspect, the present invention concerns pancreatic cells and/or pancreatic islets of the invention for the treatment of diabetes in a subject in need thereof.

The present invention also concerns a method of treating diabetes in a subject in need thereof, said method comprising steps consisting of obtaining stem cells having the capacity to differentiate into pancreatic endocrine cells;

contacting said stem cells with a SUR1/Kir6.2 channel inhibitor during their differentiation into pancreatic endocrine cells;

transplanting a therapeutically effective amount of pancreatic islets obtained by differentiation of said stem cells into said subject.

Once transplanted, the pancreatic islets begin to produce insulin, actively regulating the level of glucose in the blood. The main obstacle in islet transplantation is the fact that there is an inadequate supply of cadaveric islets to implement this procedure on a widespread clinical basis. The method of the invention solves this problem by obtaining an increase number of pancreatic islets which may be used for transplantation.

The term "diabetes" is intended to encompass type 1 and type 2 diabetes mellitus.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease.

In particular, the term "treatment of diabetes", as used herein, does not necessarily mean a complete cure but means that the symptoms or complications of the underlying disease are reduced, and/or that one or more of the underlying cellular, physiological, or biochemical causes or mechanisms causing the symptoms or complications are reduced. The term "treatment of diabetes" also includes within its scope the prophylactic treatment of an asymptomatic subject thought to be at risk of developing diabetes.

The subject to treat is any mammal, preferably a human being.

As used herein, "therapeutically effective amount" means an amount of islets administered to the subject, which will be effective to improve, prevent, delay the onset of, or treat diabetes or associated complications in the subject. Typically, it was estimated that a diabetic patient needs at least 10,000 pancreatic islets per kilogram body weight to achieve a measurable increase in insulin production. Generally, between 10,000 and 30,000 pancreatic islets per kilogram body weight are administered to the subject during transplantation. The number of pancreatic islets to be administered to a subject will vary depending on a number of parameters including the size of the subject, the severity of the disease and the site of implantation.

Generally pancreatic islets are suspended in a pharmacologically acceptable carrier, such as, for instance, cell culture medium (such as Eagle's minimal essential media), phosphate buffered saline, Krebs-Ringer buffer, and Hank's balanced salt solution +/− glucose (HBSS).

The pancreatic islets can be administered by any method known to one of skill in the art.

In an embodiment, pancreatic islets are administered by injection. For example, pancreatic islets may be administered by subcutaneous injection, intra-peritoneal injection, injection under the kidney capsule, injection through the portal vein and injection into the spleen.

According to the origin of stem cells, the islet transplantation may be autologous, isogeneic, allogeneic or xenogeneic.

As used below, the "donor" is the donor of stem cells and the "recipient" is the subject who receives the islet transplantation.

In an embodiment, the islet transplantation is isogeneic, i.e. the donor and recipient are genetically identical.

In another embodiment, the islet transplantation is allogeneic, i.e. the donor and recipient are of the same species.

In another embodiment, the islet transplantation is xenogeneic, i.e. the donor and recipient are of different species.

Allogeneic and xenogeneic transplantation require the administration of antirejection drugs.

For isogeneic, allogeneic and xenogeneic transplantation, the donor may be alive or deceased.

In a preferred embodiment, the islet transplantation is autologous, i.e. the donor and recipient are the same subject. In this case, stem cells may be (i) derived from adult tissue of the subject, (ii) derived from somatic cells of said subject which have been reprogrammed to provide induced pluripotent stem cells or (iii) from embryonic stem cells obtained by cloning.

All references cited in this specification are incorporated by reference.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps."

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

The following examples are given for purposes of illustration and not by way of limitation.

EXAMPLES

Materials and Methods

Animals and Pancreatic Dissection

Pregnant Wistar rats were purchased from the Janvier Breeding centre (CERJ, LeGenet, France). The first day post-coitum was taken as embryonic day (E) 0.5. Pregnant rats were killed with CO2 asphyxiation according to guidelines issued by the French Animal Care Committee. Dorsal pancreatic buds from E13.5 rat embryos were dissected as described previously (Miralles et al., 1998). Briefly, the stomach, pancreas and a small portion of the intestine were dissected together, and then the pancreas primordium was isolated.

Organ Culture

Dorsal pancreatic rudiments were cultured on 0.45 µm filters (Millipore) at the air-medium interface in a 35 mm sterile Petri dishes containing 2 ml RPMI-1640 medium (Invitrogen) supplemented with 100 U/ml penicillin, 100 µg/ml streptomycin, 10 mmol/L HEPES, 2 mmol/L L-glutamine, 1× non-essential aminoacids (Invitrogen) and 10% heat-inactivated fetal calf serum (HyClone, Logan, Utah, USA). Glibenclamide (MP Biomedical) and nifedipine (Sigma), used at the indicated concentrations, were first dissolved as concentrated solutions in dimethylsulfoxide DMSO (Sigma), the final concentration of DMSO in the culture medium was less than 0.5% (vol/vol). The culture medium was changed every day. Glibenclamide and nifedipine were added to the media daily. The cultures were incubated at 37° C. in a humidified atmosphere composed of 95% air and 5% CO2. At the end of the culture period, the pancreases were photographed, and fixed as described below or harvested for RNA extraction Immunochemistry and Surface Quantification Immunochemistry—The pancreatic rudiments were fixed in 10% formalin, pre-embedded in agarose gel (4% of type VII low-gelling-temperature agarose (Sigma) in H$_2$O) and embedded in paraffin. Immunohistochemistry was performed on 4-μm paraffin sections as previously described (Duvillie et al., 2006). The primary antibodies were mouse anti insulin (1/2000; Sigma), rabbit anti-glucagon (1/1000; Diasorin), rabbit anti-amylase (1/300; Sigma), rabbit anti-carboxypeptidase A (1/600; Biogenesis, Kidlington, Oxford, UK), rabbit anti-PDX1 (1/1000) (Duvillie et al., 2003) mouse anti-BrdUrd5 (1/2; Amersham Biosciences, Buckingham, UK), rabbit anti-PCK1/3, rabbit anti-Ngn3 (1/100, Guillemain et al., 2007), rabbit anti-KIR6.2 and anti-SUR1 (1/100, Santa Cruz). The fluorescent secondary antibodies were fluorescein anti-rabbit antibody (1/200; Jackson Immunoresearch, Baltimore, Md., USA), fluorescein goat anti-rabbit Alexa Fluor 488 (1/400; Invitrogen) and Texas red anti-mouse antibody (1/200; Jackson). Nuclei were stained in blue with Hoechst 33342 (0.3 μg/ml; Invitrogen). Ngn3 detection was performed as previously described (Guillemain et al., 2007) using the Vectastain elite ABC kit (Vector laboratories).

Photographs were taken using a fluorescence microscope (Leica, Leitz DMRB, Rueil-Malmaison, France) and digitized using a Hamamatsu (Middlesex, N.J.) C5810 cooled 3CCD camera.

Quantification—To quantify the surface area of insulin, glucagon, PCSK1/3, CPA and amylase-expressing cells, all sections of each pancreatic rudiment were digitized. Alternate sections were examined to avoid counting the same cell twice. The surface of insulin, glucagon, PCSK1/3, CPA, amylase, and Hoechst stainings were quantified using Iplab (Scanalytics). The stained areas were summed to obtain the total surface area per rudiment in mm$^2$. To measure proliferation of the early progenitors expressing PDX1, we counted the frequency of BrdU positive progenitors expressing PDX1 among 3000 early progenitors expressing PDX1 per rudiment. To quantify the absolute number of NGN3-expressing cells, pancreatic rudiments were sectioned and all sections were stained with an anti-NGN3 antibody. Positive cells were counted on all sections of each pancreatic rudiment. A minimum of three rudiments was analyzed per condition.

RNA Extraction and Real-Time PCR

Total RNA was isolated from pools of at least three pancreases using the Qiagen RNeasy Microkit (Qiagen, Courtaboeuf, France) and reverse transcribed using Superscript reagents (Invitrogen). Real-time PCR was performed with the 7300 Fast real-time PCR system (Applied Bio system) using either Taqman universal PCR universal PCR master mix or SYBR green PCR master mix (Applied Biosystem) with primers and labelled probes specific for each gene. Peptidylpropyl isomerase A/Cyclophilin A was used as endogenous control and E16.5 pancreas cDNA as calibrator sample. The data were analyzed by comparative cycle threshold method (Livak et al., 1997) and presented as the fold change in gene expression. At least three pools of explants were analysed by condition.

Statistical Analysis

All results are expressed as mean±sem. Statistical significance was determined using Student's t test.

Results

Figure 1B:
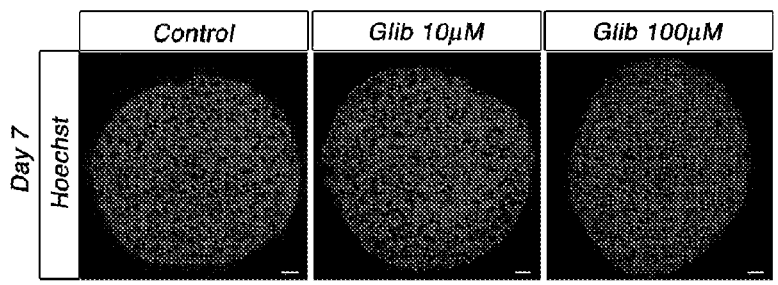
(FIG. 1B) Hoechst staining of pancreases cultured 7 days without or with the indicated concentrations of glibenclamide. Note the lack of pycnotic nuclei in glibenclamide-treated pancreases. Scale bar: 50 µm.
Figure 1C:
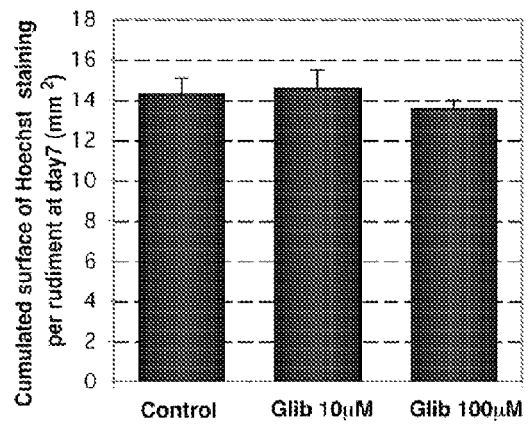
(FIG. 1C) Quantification of the absolute surface areas occupied by Hoechst staining after 7 days of culture without or with 10 and 100 µM glibenclamide. Quantification of Hoechst staining was used to estimate the size of pancreatic rudiments. Five to six pancreases were analysed for each condition. Values are means±sem.

High Concentrations of Glibenclamide did not Alter the Morphology of the Developing Pancreas In Vitro Using the in vitro model as described above (E13.5 Rat embryonic pancreases cultured at the air/medium interface on a floating filter), we examined the effects of increased concentrations of the sulphonylurea glibenclamide (an inhibitor of K$_{ATP}$ channels) on pancreas development. As shown in FIG. 1A, the pancreatic growth was similar in absence (control) or in presence of 10 nM, 100 nM, 1, 10 or 100 μM glibenclamide during the 7 days of culture. Under both conditions, the epithelium grew rapidly, spread into the mesenchyme, and developed lobules. There is no difference in apoptosis in pancreases cultured 7 days without or with 10 and 100 μM glibenclamide as shown by the Hoechst staining of the nuclei (FIG. 1B). Moreover, the lack of glibenclamide toxicity on the developing pancreas was confirmed by the quantitative analysis of the overall size of pancreases cultured 7 days in the presence or in the absence of 10 or 100 μM glibenclamide (FIG. 1C).

Based on these first results, in particular the lack of glibenclamide toxicity on the pancreas morphology, and on the effects on the pro-endocrine progenitor cells (see FIG. 4), the 100 μM glibenclamide concentration was used in the next experiments.

Effects of Glibenclamide on α and β Cells Differentiation

Figure 2A:
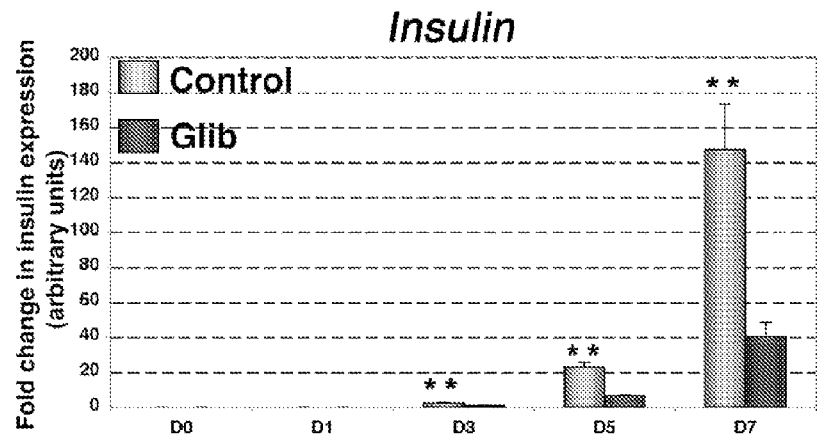
(FIG. 2A), ZnT-8 (FIG. 2B) and MafA (FIG. 2C). mRNA in E13.5 pancreases before (D0) and after 1, 3, 5 and 7 days of culture (D1, D3, D5 and D7 respectively) with or without 100 µM glibenclamide. Each data point represents the mean±sem of at least six independent experiments **, p<0.01.
Figure 2B:
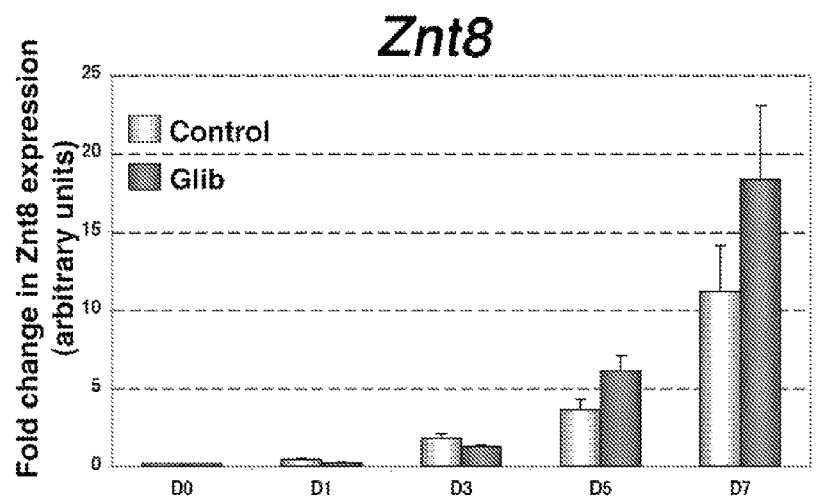
FIG. 2: Effects of glibenclamide on β and α cell differentiation.
(FIG. 2D) Quantification of the absolute surface area occupied by proprotein convertase subtilisin/kexin 1/3 (PCSK1/3) staining in PDX-1-expressing cells that developed after 7 days of culture in presence or in absence of 100 µM glibenclamide. Values are means±sem of at least three independent experiments.
(FIG. 2E) The absolute surface of glucagon staining in E13.5 pancreases cultured 7 days in presence or in absence of 100 µM glibenclamide was quantified. Values are means±sem of at least three independent experiments , p<0.01.
(FIG. 2F) Expression profile of Pou3F4 by real-time PCR in E13.5 pancreases before (D0) and after 1, 3, 5 and 7 days of culture (D1, D3, D5 and D7 respectively) in the presence or in absence of 100 µM glibenclamide. Each data point represents the mean±sem of at least three independent experiments , p<0.01.
Figure 2C:
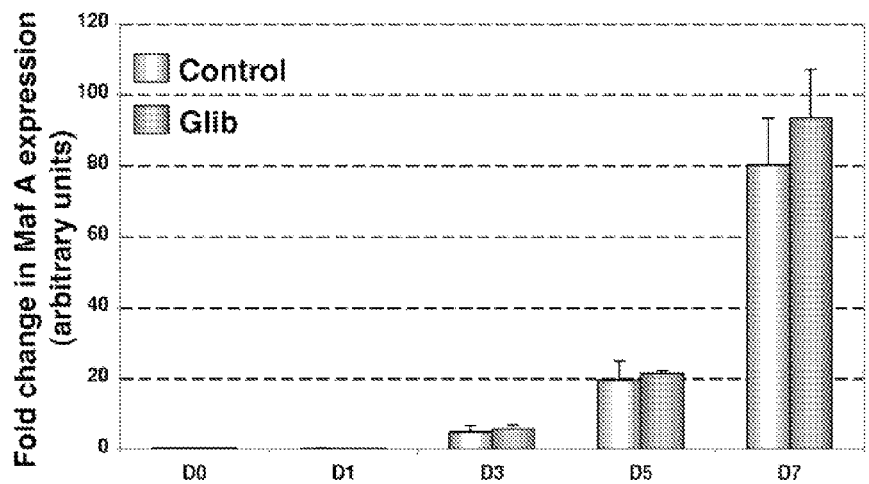
Figure 2D:
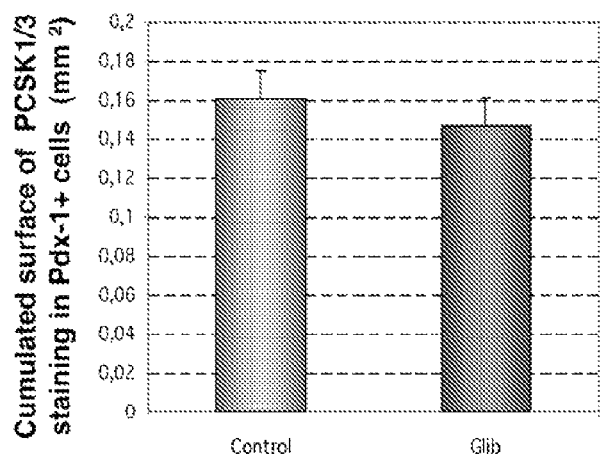

To determine the effects of glibenclamide on endocrine development and in particular in cells expressing SUR1, the number of insulin-positive cells in pancreases grown for 7 days in the absence or the presence of glibenclamide was compared. The glibenclamide treated-explants exhibit a very few insulin positive cells and the surface area occupied by the insulin-cell population was decreased by 70% (data not shown). Because glibenclamide is a potent insulin secretagogue, the inventors asked if the observed low insulin content was only the consequence of increased insulin secretion in the culture medium or was due to the reduced insulin mRNA level. To test this latter hypothesis, they analysed by real-time PCR the expression of insulin gene before (D0) and after 1, 3, 5 and 7 days of culture. As shown in FIG. 2A, the insulin expression was strongly reduced in the glibenclamide-treated pancreases as early as D3. Two mechanisms can account for the observed decrease in insulin expression: (i) inhibition of the β-cell differentiation from the pro-endocrine progenitors leading to a reduction of the β-cell number and thus to a decrease in overall amount of insulin mRNA or (ii) inhibition of the insulin gene without affecting the β-cell population. Thus, the expression pattern of two β-cell markers: the zinc transporter ZnT-8 (Chimienti et al., 2004) and the β-cell specific transcription factor MafA (Zhang et al., 2005; Matsuoka et al., 2007) was examined (FIGS. 2B and 2C). These results indicate that over the 7 days of culture, glibenclamide did not affect the expression of these two beta-cells markers. Moreover, after 7 days of culture, the surface area occupied by the pro-hormone convertase 1/3 (PCSK1/3) staining in PDX-1+ cells (Pdx-1 is specifically expressed in the adult β-cell (Ohlsson et al., 1993)) was similar in pancreases cultured without or with glibenclamide (FIG. 2D). These results demonstrate that high concentrations of glibenclamide do not prevent the β-cell differentiation.

Figure 2E:
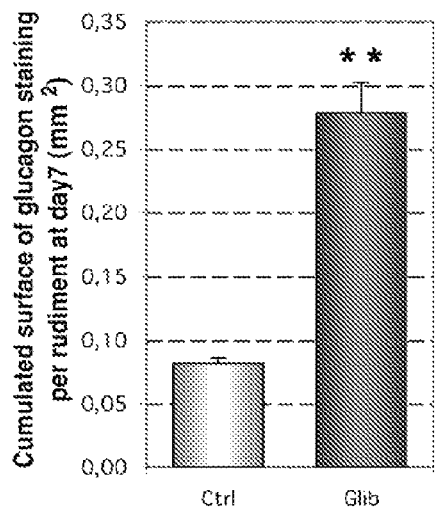
Figure 2F:
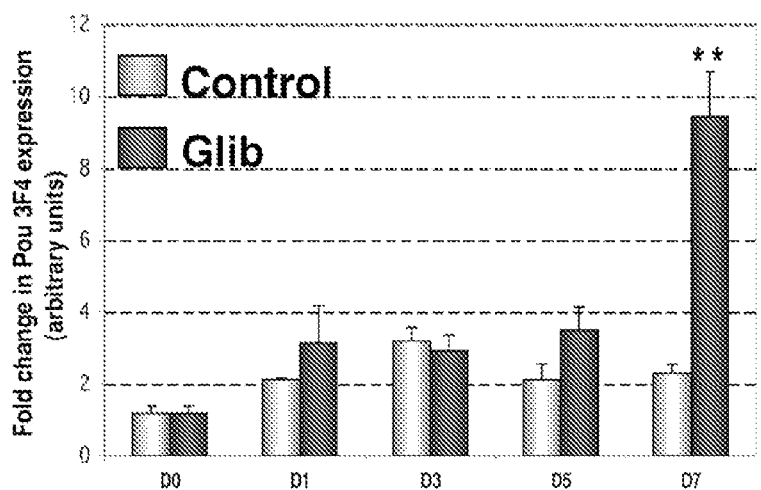

It was further observed that glibenclamide increased by 3.5 fold the number of glucagon-expressing cells (FIG. 2E). Moreover, this result was confirmed by the significant increase of Pou3F4/Brn4 mRNA level at D7 (FIG. 2F); Pou3F4, known as the only α-cell specific transcription factor which maintains the α cell fate (Jensen et al., 2000; Heller et al., 2004). In the other hand, we found also a two-fold increase in somatostatin expression after 7 days of culture in the glibenclamide-treated pancreas (data not shown).

Figure 3A:
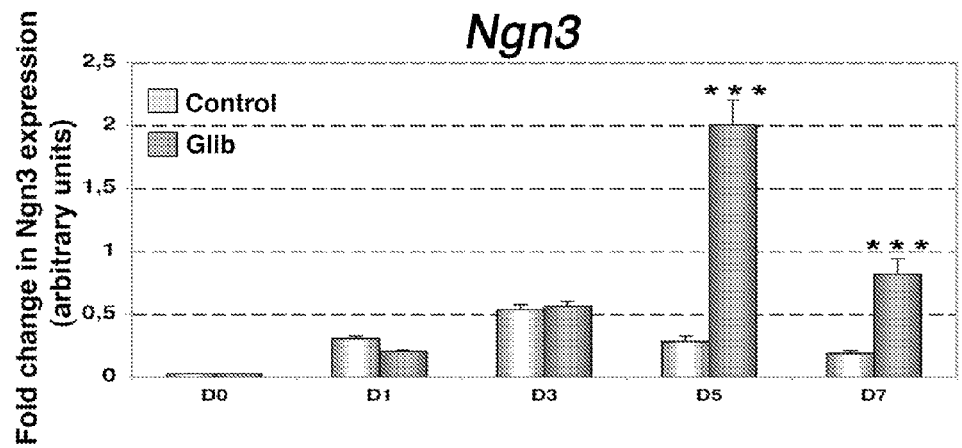
(FIG. 3A) Quantification by real-time PCR of Ngn3 transcripts in E13.5 pancreases after 0, 1, 3, 5 and 7 days of culture (D0, D1, D3, D5 and D7 respectively) with or without 100 µM glibenclamide. Each data point represents the mean±sem of at least seven independent experiments *, p<0.001.

Glibenclamide Amplifies the Pool of Endocrine Progenitors, Increases the Expression of the Ngn3 Target but does Not Affect the Proliferation of Pancreatic Precursors The pancreatic endocrine fate is determined by the expression of Ngn3, a transcription factor which specifically labels the endocrine precursors (Gradwohl et al., 2000; Gu et al., 2002). The expression pattern of Ngn3 was investigated before and after 1, 3, 5 and 7 days of culture. As shown in FIG. 3A, Ngn3 was weakly expressed at E13.5 (D0). It increases at day 1 and 3 but remain similar in absence or in presence of glibenclamide. In contrast, after 5 days of culture, Ngn3 expression reached a peak and was sevenfold increased by glibenclamide (*: p<0.001). Thereafter, Ngn3 mRNA level decreased slightly but remained dramatically higher (*: p<0.001) in the glibenclamide-treated pancreases.

Figure 3B:
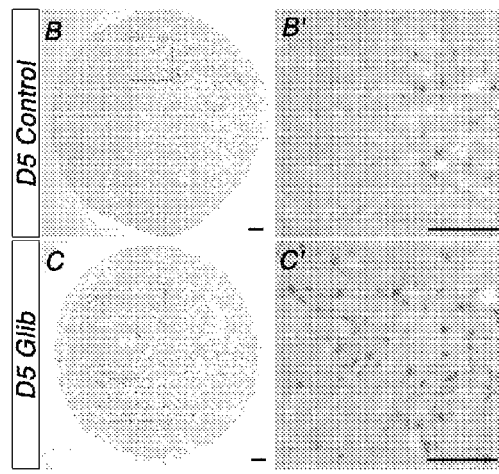
(FIG. 3B): Immunohistochemistry analysis of NGN3 expression in E13.5 pancreases cultured 5 days in presence (C, C') or in absence (B, B') of 100 µM glibenclamide. Note the increased number of NGN3 positive nuclei in the glibenclamide-treated explants. Scale bar: 50 µm. B' and C' are respectively the enlargement of B and C.
Figure 3C:
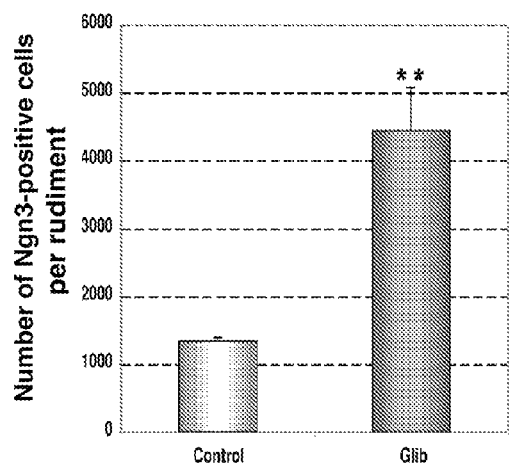
(FIG. 3C) Quantification of the number of NGN3 positive-cells in E13.5 pancreases cultured for 5 days in presence or in absence of 100 µM glibenclamide. Values are means±sem of at least three independent experiments , p<0.01.

To test whether glibenclamide acts not only on Ngn3 gene expression but also on NGN3-expressing cell number, NGN3 expression was analysed by immunohistochemistry (FIG. 3B) and the number of NGN3+ cells was compared in pancreases cultured for 5 days in absence or in presence of glibenclamide. FIG. 3C shows that the number of NGN3+ cells that develop in presence of glibenclamide was threefold higher than in absence of glibenclamide. These results indicate that glibenclamide amplifies the pool of NGN3+ endocrine progenitors.

Because the transcription factor NeuroD1/Beta2 is a downstream target of Ngn3 (Huang et al., 2000) and is necessary to the endocrine differentiation (Guillemain et al., 2007); the inventors examined the expression pattern of this target of Ngn3. mRNA levels were similar after 1 and 3 days of culture in absence or in presence of glibenclamide. In concordance with the expression pattern of Ngn3 in the glibenclamide-treated pancreases, NeuroD1 was significantly increased at D5 and reminded enhanced at D7 (data not shown). These results demonstrate that the overexpression of Ngn3 leads to the induction of a key factor important for islet differentiation.

Figure 3D:
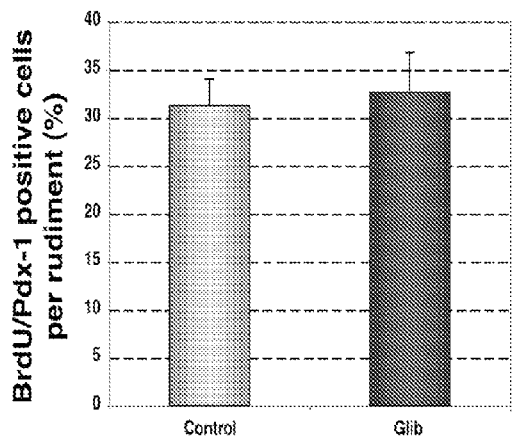
(FIG. 3D) E13.5 pancreases were grown for 24 h with or without 100 µM glibenclamide and pulsed with BrdU during the last hour of culture. Immunohistochemistry was performed using anti-PDX1 and anti-BrdU antibodies. Quantification of the proliferation of early PDX1 progenitors in pancreases cultured 24 h in the absence or presence of 100 µM glibenclamide

Furthermore, embryonic pancreases were cultured for 1 day and BrdU was added during the last hour of culture to test whether glibenclamide increased Ngn3+ cell number by acting on pancreatic progenitor cell proliferation. The percentage of PDX-1+ cells that incorporate BrdU was similar in presence (32.60%±4.2%) or in absence (31.24%±2.8%) of glibenclamide (FIG. 3D). These results demonstrate that glibenclamide does not modify the pancreatic precursor proliferation.

In conclusion, glibenclamide amplifies the pool of pro-endocrine cells expressing Ngn3 without acting on the pancreatic progenitor proliferation.

NGN3+ Cells Induced by Glibenclamide Differentiate into Beta Cells

Figure 4A:
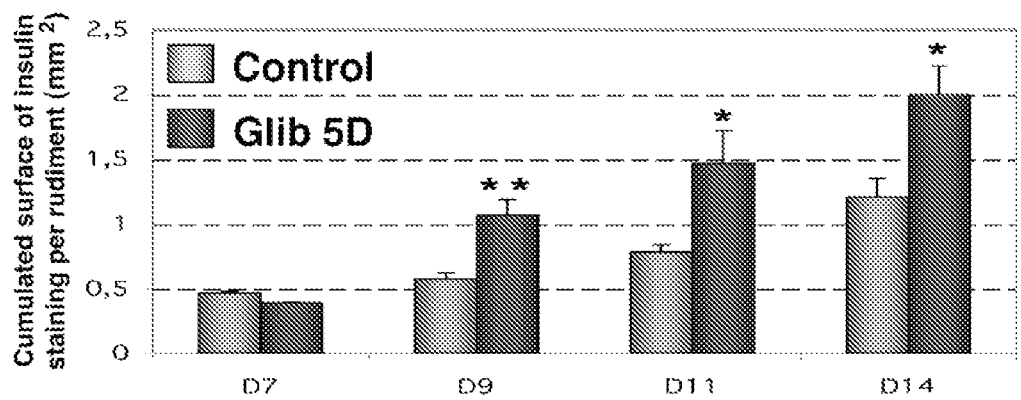
(FIG. 4A) Quantification of the absolute surface area occupied by insulin staining in β cells that developed after 7, 9, 11 and 14 days of culture in absence or in presence of 100 µM glibenclamide only during the first 5 days of culture. Each data point represents the mean±sem of at least three independent experiments *, p<0.05; , p<0.01.

Pancreases were cultured up to 14 days in presence of glibenclamide only during the first 5 days of culture, i.e until Ngn3 reaches a peak (Glib-5D pancreases), in absence (Control pancreases) or in presence of glibenclamide (Glib pancreases) during the 14-day culture period. Then, the insulin-expressing cell masses were compared after 9, 11 and 14 days of culture. As shown in FIG. 4A, a large number of insulin-expressing cells was observed in Glib-5D pancreases at D 9, D11 or D14. In contrast, less insulin-containing cells were detected in Glib pancreases (data not shown). Such an inhibitory effect of glibenclamide on insulin expression and content without affecting the beta cell number has been already mentioned above (see FIG. 2).

Figure 4B:
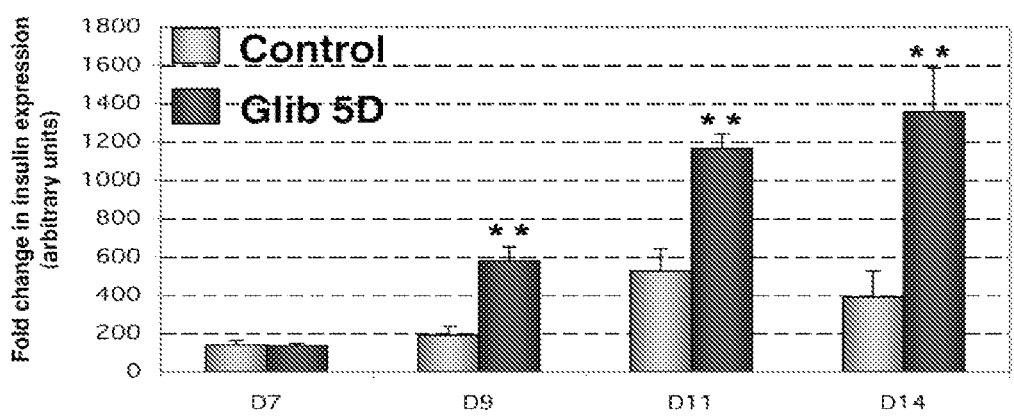
(FIG. 4B) Quantification by real-time PCR of insulin transcripts in E13.5 pancreases after 7, 9, 11 and 14 days of cultured without or with 100 µM glibenclamide only during the first 5 days of culture. Each data point represents the mean±sem of at least three independent experiments , p<0.01. Quantification by real-time PCR of ZnT-8 (FIG. 4C) and MafA (FIG. 4D) transcripts in E13.5 pancreases after 7, 9, 11 and 14 days of cultured without or with 100 µM glibenclamide only during the first 5 days of culture. Each data point represents the mean±sem of at least three independent experiments **, p<0.01.

By real real-time PCR, the insulin expression was assessed after 7, 9, 11 and 14 days of culture. As shown in FIG. 4B, while insulin mRNA levels in control and Glib-5D pancreases were identical at D7, the insulin mRNA level of Glib-5D pancreases increased by threefold at D9, twofold at D11 and threefold at D14 when compared with control pancreases. This result was further confirmed by the quantification of insulin-staining area (data not shown) which revealed a significant increase of insulin-positive cells in Glib 5D pancreases.

Figure 4C:
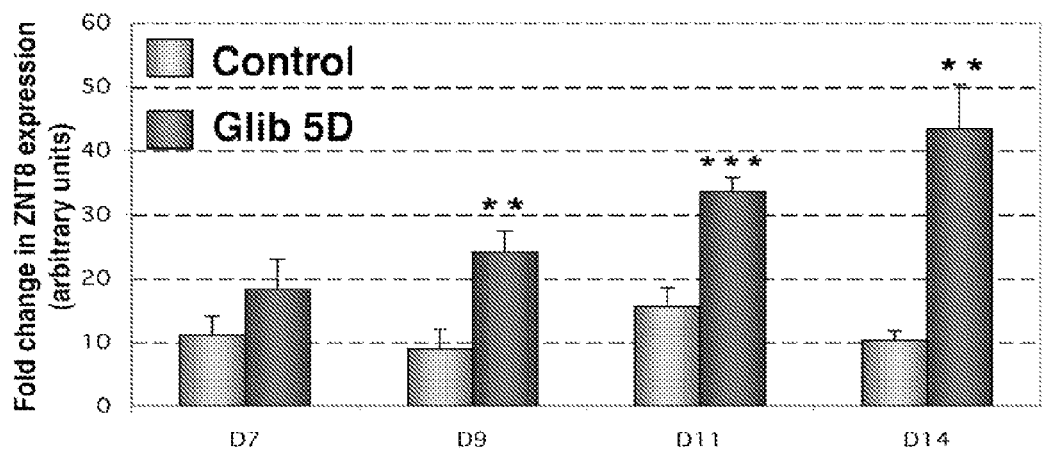
FIG. 4: Glibenclamide-induced NGN3+ cells differentiate into β cells.
Figure 4D:
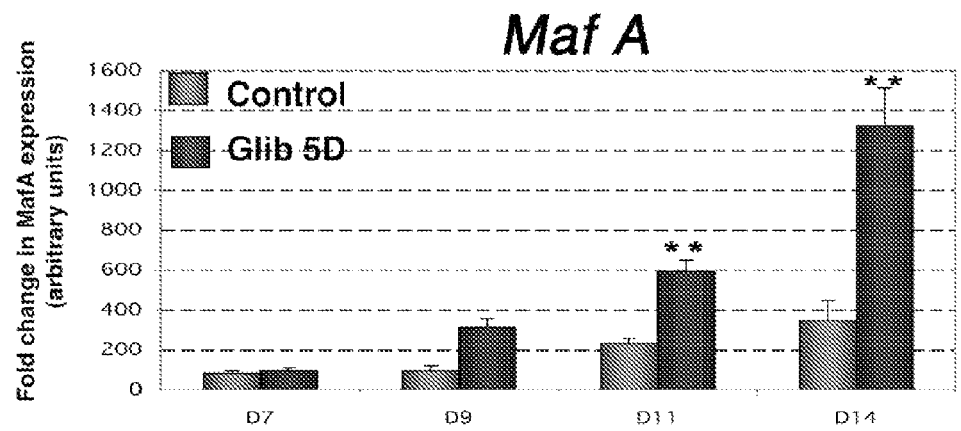

To verify that the strong activation of insulin expression, along with the increase of insulin-positive cells observed in Glib 5D pancreases, were correlated to an increase of β-cell differentiation, the expression patterns of the two beta-cell markers ZnT-8 and MafA were analyzed at D7, D9, D11 and D14. As shown in FIGS. 4C and 4D, whereas the ZnT-8 and MafA expression in Glib-5D and control pancreases were similar after 7 days of culture, a dramatic increase (p<0.01) of the expression of these two β-cell markers was observed after 9, 11 and 14 days of culture in Glib 5D pancreases suggesting that β-cell number is increased by glibenclamide treatment.

Thus, these results demonstrate that glibenclamide-induced NGN3+ cells have the ability to differentiate in β-cells.

CONCLUSION

The inventors demonstrated that a SUR1/Kir6.2 channel inhibitor, namely glibenclamide, was able to expand significantly the pool of the endocrine progenitor NGN3$^+$ cells that further differentiate into pancreatic endocrine cells thus leading to a final increase of the beta cell mass and insulin expression, without inducing any deleterious effects in the developing pancreas.

REFERENCES

Assady S, Maor G, Amit M, Itskovitz-Eldor J, Skorecki K L, Tzukerman M. Insulin production by human embryonic stem cells. Diabetes. 50(8):1691-7, 2001

Bonner-Weir S, Inada A, Yatoh S, Li W C, Aye T, Toschi E, Sharma A: Transdifferentiation of pancreatic ductal cells to endocrine beta-cells. Biochem Soc Trans. 36(3):353-6, 2008

Chimienti F, Devergnas S, Favier A, Seve M: Identification and cloning of a beta-cell-specific zinc transporter, ZnT-8, localized into insulin secretory granules. Diabetes 53:2330-2337, 2004

Duvillie B, Attali M, Aiello V, Quemeneur E, Scharfmann R: Label-retaining cells in the rat pancreas: location and differentiation potential in vitro. Diabetes 52:2035-2042, 2003

Duvillie B, Attali M, Bounacer A, Ravassard P, Basmaciogullari A, Scharfmann R: The mesenchyme controls the timing of pancreatic beta-cell differentiation. Diabetes 55:582-589, 2006

Gabr M M, Sobh M M, Zakaria M M, Refaie A F, Ghoneim M A: Transplantation of insulin-producing clusters derived from adult bone marrow stem cells to treat diabetes in rats. Exp Clin Transplant. 6(3):236-43, 2008

Gradwohl G, Dierich A, LeMeur M, Guillemot F: neurogenin3 is required for the development of the four endocrine cell lineages of the pancreas. Proc Natl Acad Sci USA 97:1607-1611, 2000

Gu G, Dubauskaite J, Melton D A: Direct evidence for the pancreatic lineage: NGN3+ cells are islet progenitors and are distinct from duct progenitors. Development 129:2447-2457, 2002

Guillemain G, Filhoulaud G, Da Silva-Xavier G, Rutter G A, Scharfmann R: Glucose is necessary for embryonic pancreatic endocrine cell differentiation. J Biol Chem 282: 15228-15237, 2007

Heller R S, Stoffers D A, Liu A, Schedl A, Crenshaw E B, 3rd, Madsen O D, Serup P: The role of Brn4/Pou3f4 and Pax6 in forming the pancreatic glucagon cell identity. Dev Biol 268:123-134, 2004

Hod Y, Gu X, Xie X, Kim S K: Differentiation of insulin-producing cells from human neural progenitor cells. PLoS Med. 2(4):e103, 2005

Huang H P, Liu M, El-Hodiri H M, Chu K, Jamrich M, Tsai M J: Regulation of the pancreatic islet-specific gene BETA2 (neuroD) by neurogenin 3. Mol Cell Biol 20:3292-3307, 2000

Hyde K, Reid C J, Tebbutt S J, Weide L, Hollingsworth M A, Harris A: The cystic fibrosis transmembrane conductance regulator as a marker of human pancreatic duct development. Gastroenterology 113:914-919, 1997

Jensen J, Heller R S, Funder-Nielsen T, Pedersen E E, Lindsell C, Weinmaster G, Madsen O D, Serup P: Independent development of pancreatic alpha- and beta-cells from neurogenin3-expressing precursors: a role for the notch pathway in repression of premature differentiation. Diabetes 49:163-176, 2000

Kilic G, Wang J, Sosa-Pineda B: Osteopontin is a novel marker of pancreatic ductal tissues and of undifferentiated pancreatic precursors in mice. Dev Dyn 235:1659-1667, 2006

Kodama S, Kühtreiber W, Fujimura S, Dale E A, Faustman D L: Islet regeneration during the reversal of autoimmune diabetes in NOD mice. Science. 302(5648):1223-7, 2003

Livak K J, Schmittgen T D: Analysis of relative gene expression data using real-time quantitative PCR and the 2(-Delta Delta C(T)) Method. Methods 25:402-408, 2001

Lowry W E, Richter L, Yachechko R, Pyle A D, Tchieu J, Sridharan R, Clark A T, Plath K. Generation of human induced pluripotent stem cells from dermal fibroblasts. Proc Natl Acad Sci USA. 105(8):2883-8, 2008

Maherali et al., Guidelines and techniques for the generation of induced pluripotent stem cells. Cell Stem Cell, 3(6):595-605, 2008

Matsuoka T A, Kaneto H, Stein R, Miyatsuka T, Kawamori D, Henderson E, Kojima I, Matsuhisa M, Hori M, Yamasaki Y: MafA regulates expression of genes important to islet beta-cell function. Mol Endocrinol 21:2764-2774, 2007

Miralles F, Czernichow P, Scharfmann R: Follistatin regulates the relative proportions of endocrine versus exocrine tissue during pancreatic development. Development 125: 1017-1024, 1998

Moriscot C, de Fraipont F, Richard M J, Marchand M, Savatier P, Bosco D, Favrot M, Benhamou P Y: Human bone marrow mesenchymal stem cells can express insulin and key transcription factors of the endocrine pancreas developmental pathway upon genetic and/or microenvironmental manipulation in vitro. Stem Cells. 23(4):594-603, 2005

Oh S H, Muzzonigro T M, Bae S H, LaPlante J M, Hatch H M, Petersen B E: Adult bone marrow-derived cells trans-differentiating into insulin-producing cells for the treatment of type I diabetes. Lab Invest. 84(5):607-17, 2004

Ohlsson H, Karlsson K, Edlund T: IPF1, a homeodomain-containing transactivator of the insulin gene. Embo J 12:4251-4259, 1993

Park S P, Lee Y J, Lee K S, Ah Shin H, Cho H Y, Chung K S, Kim E Y, Lim J H. Establishment of human embryonic stem cell lines from frozen-thawed blastocysts using STO cell feeder layers. Hum Reprod. 19(3):676-84, 2004

Qi M, Strand B L, Morch Y, Lacik I, Wang Y, Salehi P, Barbaro B, Gangemi A, Kuechle J, Romagnoli T, Hansen M A, Rodriguez L A, Benedetti E, Hunkeler D, Skjak-Braek G, Oberholzer J. Encapsulation of human islets in novel inhomogeneous alginate-ca2+/ba2+ microbeads: in vitro and in vivo function. Artif Cells Blood Substit Immobil Biotechnol. 36(5):403-20, 2008

Romano G: Artificial reprogramming of human somatic cells to generate pluripotent stem cells: A possible alternative to the controversial use of human embryonic stem cells. Drug News Perspect. 21(8): 440-5, 2008

Sapir T, Shternhall K, Meivar-Levy I, Blumenfeld T, Cohen H, Skutelsky E, Eventov-Friedman S, Barshack I, Goldberg I, Pri-Chen S, Ben-Dor L, Polak-Charcon S, Karasik A, Shimon I, Mor E, Ferber S: Cell-replacement therapy for diabetes: Generating functional insulin-producing tissue from adult human liver cells. Proc Natl Acad Sci USA. 102(22):7964-9, 2005

Seaberg R M, Smukler S R, Kieffer T J, Enikolopov G, Asghar Z, Wheeler M B, Korbutt G, van der Kooy D: Clonal identification of multipotent precursors from adult mouse pancreas that generate neural and pancreatic lineages. Nat Biotechnol. 22(9):1115-24, 2004

Sun Y, Chen L, Hou X G, Hou W K, Dong J J, Sun L, Tang K X, Wang B, Song J, Li H, Wang K X: Differentiation of bone marrow-derived mesenchymal stem cells from diabetic patients into insulin-producing cells in vitro. Chin Med J (Engl). 120(9):771-6, 2007

Takahashi K, Tanabe K, Ohnuki M, Narita M, Ichisaka T, Tomoda K, Yamanaka S. Induction of pluripotent stem cells from adult human fibroblasts by defined factors. Cell. 131(5):861-72, 2007

Tateishi K, He J, Taranova O, Liang G, D'Alessio A C, Zhang Y. Generation of insulin-secreting islet-like clusters from human skin fibroblasts. J Biol Chem. 283(46):31601-7, 2008

Timper K, Seboek D, Eberhardt M, Linscheid P, Christ-Crain M, Keller U, Müller B, Zulewski H: Human adipose tissue-derived mesenchymal stem cells differentiate into insulin, somatostatin, and glucagon expressing cells. Biochem Biophys Res Commun. 341(4):1135-40, 2006

Yang L, Li S, Hatch H, Ahrens K, Cornelius J G, Petersen B E, Peck A B: In vitro trans-differentiation of adult hepatic stem cells into pancreatic endocrine hormone-producing cells. Proc Natl Acad Sci USA. 99(12):8078-83, 2002

Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. Induced pluripotent stem cell lines derived from human somatic cells. Science. 318(5858):1917-20, 2007

Zhang C, Moriguchi T, Kajihara M, Esaki R, Harada A, Shimohata H, Oishi H, Hamada M, Morito N, Hasegawa K, Kudo T, Engel J D, Yamamoto M, Takahashi S: MafA is a key regulator of glucose-stimulated insulin secretion. Mol Cell Biol 25:4969-4976, 2005

The invention claimed is:

1. An in vitro method for increasing the pool of Ngn3$^+$ endocrine progenitor cells obtained from stem cells, wherein said method comprises the step of contacting stem cells having the capacity to differentiate into pancreatic endocrine cells with a SUR1/Kir6.2 channel inhibitor.

2. The method according to claim 1, further comprising a step consisting of the differentiation of said Ngn3$^+$ endocrine progenitor cells into precursors of pancreatic endocrine cells and/or pancreatic endocrine cells.

3. The method according to claim 1, wherein the SUR1/Kir6.2 channel inhibitor is selected from the group consisting of sulfonylureas, meglitinides and combinations thereof.

4. The method according to claim 3, wherein the SUR1/Kir6.2 channel inhibitor is glibenclamide.

5. The method according to claim 1, wherein stem cells are selected from the group consisting of pancreatic stem cells, pluripotent stem cells and multipotent stem cells.

6. The method according to claim 5, wherein pancreatic stem cells are selected from the group consisting of stem cells derived from pancreatic islets, pancreatic ducts or pancreatic acinar cells and stem cells derived from the dorsal pancreatic bud from non-human embryos.

7. The method according to claim 5, wherein multipotent stem cells are derived from adult tissue selected from the group consisting of bone marrow, liver, central nervous system, spleen and adipose tissue.

8. The method according to claim 5, wherein pluripotent stem cells are derived from non-human embryonic stem cells or are obtained by reprogramming of somatic cells.

9. The method according to claim 1, wherein stem cells are contacted with a SUR1/Kir6.2 channel inhibitor for 3 to 10 days.

10. The method according to claim 1, wherein stem cells are contacted with a SUR1/Kir6.2 channel inhibitor by culturing them in presence of 0.1 to 500 μM of said inhibitor.

* * * * *

UNITED STATES PATENT AND TRADEMARK OFFICE
CERTIFICATE OF CORRECTION

| | | |
|---|---|---|
| PATENT NO. | : 8,679,842 B2 | Page 1 of 1 |
| APPLICATION NO. | : 13/203019 | |
| DATED | : March 25, 2014 | |
| INVENTOR(S) | : Michel Polak et al. | |

It is certified that error appears in the above-identified patent and that said Letters Patent is hereby corrected as shown below:

In The Specification

<u>Column 17,</u>
Line 1, "Hod Y," should read --Hori Y,--.

Signed and Sealed this
Twentieth Day of January, 2015

Michelle K. Lee
*Deputy Director of the United States Patent and Trademark Office*